US012569178B2

(12) United States Patent
Yoshino et al.

(10) Patent No.: US 12,569,178 B2
(45) Date of Patent: Mar. 10, 2026

(54) ELECTRODE

(71) Applicant: TATSUTA ELECTRIC WIRE & CABLE CO., LTD., Higashiosaka (JP)

(72) Inventors: Shinji Yoshino, Higashiosaka (JP); Koujirou Ikoma, Higashiosaka (JP)

(73) Assignee: TATSUTA ELECTRIC WIRE & CABLE CO., LTD., Higashiosaka (JP)

( * ) Notice: Subject to any disclaimer, the term of this patent is extended or adjusted under 35 U.S.C. 154(b) by 716 days.

(21) Appl. No.: 17/766,072

(22) PCT Filed: Jun. 19, 2020

(86) PCT No.: PCT/JP2020/024205
§ 371 (c)(1),
(2) Date: Apr. 1, 2022

(87) PCT Pub. No.: WO2021/070418
PCT Pub. Date: Apr. 15, 2021

(65) Prior Publication Data
US 2022/0346689 A1 Nov. 3, 2022

(30) Foreign Application Priority Data

Oct. 11, 2019 (JP) ................................ 2019-187718

(51) Int. Cl.
*A61B 5/265* (2021.01)
(52) U.S. Cl.
CPC ...... *A61B 5/265* (2021.01); *A61B 2562/0215* (2017.08)

(58) Field of Classification Search
CPC ........................ A61B 5/265; A61B 2562/0215
See application file for complete search history.

(56) References Cited

U.S. PATENT DOCUMENTS

| | | | |
|---|---|---|---|
| 5,078,138 A * | 1/1992 | Strand .................... | A61B 5/259 600/372 |
| 9,391,423 B2 * | 7/2016 | Bulovic ................. | H01S 3/094 |
| 2002/0115920 A1 * | 8/2002 | Rich .................... | A61B 5/6862 600/549 |
| 2003/0045788 A1 * | 3/2003 | Menon ................... | A61B 5/259 600/395 |
| 2004/0069654 A1 | 4/2004 | McLaughlin et al. | |

(Continued)

FOREIGN PATENT DOCUMENTS

| | | |
|---|---|---|
| JP | S55134101 A | 10/1980 |
| JP | 2004512527 A | 4/2004 |

(Continued)

OTHER PUBLICATIONS

Mafune, T, Translation of WO 2017159136-A1 (Year: 2017).*
Takemori, Saatoru, Translation of WO-2017159136-A1, 2017 (Year: 2017).*

*Primary Examiner* — Adam Z Minchella
(74) *Attorney, Agent, or Firm* — The Webb Law Firm

(57) ABSTRACT

Provided is an electrode including: a polarizable electrode layer; and a non-polarizable electrode layer laminated on the polarizable electrode layer. The non-polarizable electrode layer includes silver, silver chloride, and a corrosion inhibitor for the silver. The corrosion inhibitor is a polymer-based corrosion inhibitor.

7 Claims, 5 Drawing Sheets

(56)                    References Cited

U.S. PATENT DOCUMENTS

2005/0131336 A1*   6/2005   Mori ................... A61N 1/0492
                                                                   604/20
2007/0205701 A1*   9/2007   Grumm ............... A61B 5/4818
                                                                   310/800
2013/0011666 A1    1/2013   Mochizuki
2019/0142295 A1    5/2019   Shinohara et al.

FOREIGN PATENT DOCUMENTS

JP          2005503189 A       2/2005
JP          201988764 A        6/2019
WO          02089906 A2        11/2002
WO          03061758 A1        7/2003
WO          2011122241 A1      10/2011
WO       WO-2017159136 A1 *    9/2017    .......... G06F 3/0445

* cited by examiner

ELECTRODE

CROSS-REFERENCE TO RELATED APPLICATIONS

This application is the United States national phase of International Application No. PCT/JP2020/024205 filed Jun. 19, 2020, and claims priority to Japanese Patent Application No. 2019-187718 filed Oct. 11, 2019, the disclosures of which are hereby incorporated by reference in their entirety.

BACKGROUND OF THE INVENTION

Field of the Invention

The present invention relates to an electrode, particularly to a biological electrode.

Description of Related Art

Conventionally used has been an electrode including: a polarizable electrode layer; and a non-polarizable electrode layer including silver and silver chloride. Such an electrode has silver and silver chloride exhibiting excellent non-polarizability, and is thus suitable for use as a biological electrode (see Patent Literature 1).

Also proposed has been an electrode including a non-polarizable electrode layer formed of a thin film of silver on a surface of a polarizable electrode layer by the thin film forming method such as silver vapor deposition (see Patent Literature 2). Such an electrode has an advantage of being produced at low costs since the amount of silver used can be reduced by employing the thin film forming method.

CITATION LIST

Patent Literature

Patent Literature 1: WO 2003/061758 A
Patent Literature 2: JP 2004-512527 T

SUMMARY OF THE INVENTION

Technical Problem

The electrode described in Patent Literature 2 makes it possible to reduce the amount of silver used, but has a problem of deteriorating the thin film of silver and degrading its performance during storage. In particular, a biological electrode, in which a conductive gel layer as a layer brought into contact with skin is generally attached to the non-polarizable electrode layer, has a problem that chloride ions or the like included in the conductive gel layer causes silver to be easily deteriorated during storage.

In view of the above problems, it is an object of the present invention to provide an electrode excellent in storage stability and capable of reducing the amount of silver used.

Solution to Problem

An electrode according to the present invention includes: a polarizable electrode layer; and a non-polarizable electrode layer laminated on the polarizable electrode layer, in which the non-polarizable electrode layer includes silver, silver chloride, and a corrosion inhibitor for the silver, and the corrosion inhibitor is a polymer-based corrosion inhibitor.

The electrode according to the present invention is preferably configured such that the corrosion inhibitor includes a resin and a thermosetting agent.

The electrode according to the present invention is preferably configured such that the resin includes a polyester-based resin.

The electrode according to the present invention is preferably configured such that the thermosetting agent includes an isocyanate-based thermosetting agent.

The electrode according to the present invention is preferably configured such that the non-polarizable electrode layer includes a plating film of the silver formed on a surface of the polarizable electrode layer.

The electrode according to the present invention is preferably a biological electrode.

DESCRIPTION OF THE INVENTION

A description will be hereinafter given on an electrode 1 according to one embodiment of the present invention with reference to the drawings.

The electrode 1 of this embodiment is a biological electrode used for acquiring biological information. Examples of biological information include electrocardiogram, electroencephalography, and electromyography. The electrode 1 is used for acquiring such information, and thus preferably has such flexibility as to be capable of being attached along the surface of skin. In terms of its performance as a biological electrode, the electrode 1 has preferably a small impedance, which is, for example, $2000\Omega$ or less, $1000\Omega$ or less, $500\Omega$ or less. Further, it is preferable that the electrode 1 be capable of maintaining such performance at room temperature for 2 years or more. For example, in an acceleration test, it is preferable that the electrode 1 be capable of maintaining the above performance at a temperature of $57°$ C. for 3 weeks or more, 5 weeks or more, 7 weeks or more, or 10 weeks or more.

Figure 1A:
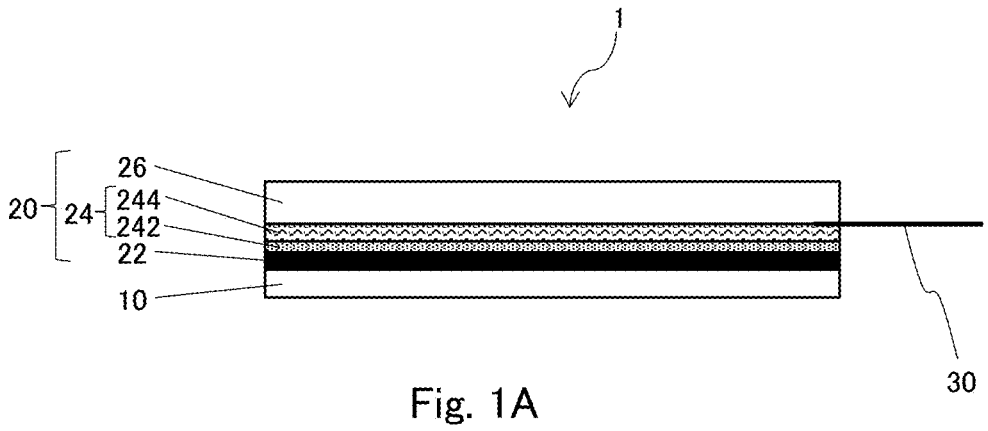
FIG. 1A is a schematic view showing a sectional structure of an electrode according to one embodiment.

As shown in FIG. 1A, the electrode 1 includes a substrate 10 having a sheet shape, an electrode layer 20 laminated on one surface of the substrate 10 and used for detecting electrical signals from a living body, and a lead wire 30 electrically connected to the electrode layer 20.

The substrate 10 is generally formed of an electrically insulating film made of polyethylene terephthalate (PET). An electrically insulating film herein refers to a film having a volume resistivity of $1\times10^{13}\Omega\cdot cm$ or more. The thickness of the substrate 10 is generally set to 5 to 100 μm.

The electrode layer 20 includes a polarizable electrode layer 22 formed on one surface of the substrate 10, a non-polarizable electrode layer 24 formed on a surface of the polarizable electrode layer 22, and a conductive gel layer 26 formed on a surface of the non-polarizable electrode layer 24.

In this embodiment, the polarizable electrode layer 22 is formed of a carbon paste including graphite and/or carbon powder in addition to a resin.

The thickness of the polarizable electrode layer 22 is generally set to 2 to 100 µm, preferably to 3 to 50 µm, further preferably to 4 to 20 µm.

The non-polarizable electrode layer 24 includes a silver and silver chloride layer 242 formed on a surface of the polarizable electrode layer 22, and a corrosion prevention layer 244 formed to cover the silver and silver chloride layer 242 for suppressing silver from corrosion.

In this embodiment, the silver and silver chloride layer 242 is formed by forming a silver thin film on the surface of the polarizable electrode layer 22 by the thin film forming method, followed by converting a part of silver into silver chloride through chlorination treatment. The silver thin film is preferably a plating film. Further, as the chlorination treatment, a method by immersion in an aqueous sodium hypochlorite solution is preferable. Thereby, the presence of silver and silver chloride in a uniform state in a direction in which a surface extends allows the electrode to maintain its function even when the amount of silver used is reduced to suppress the production cost of the electrode 1. More specifically, a uniform silver thin film is formed by the thin film forming method across the entire surface of the polarizable electrode layer 22, and the entire polarizable electrode layer 22 on which the silver thin film is formed is immersed in an aqueous sodium hypochlorite solution to thereby allow hypochlorous acid to penetrate the silver thin film and uniformly form silver chloride in the silver thin film.

The non-polarizable electrode layer 24 of this embodiment having the corrosion prevention layer 244 formed therein suppresses deterioration of silver and maintains its non-polarizability even when the silver and silver chloride layer 242 is formed thinly to reduce the amount of silver used. Specifically, the thickness of the silver and silver chloride layer 242 is, for example, 0.05 to 3.0 µm, preferably 0.05 to 1.0 µm, more preferably 0.05 to 0.5 µm, further preferably 0.05 to 0.35 µm, still further preferably 0.08 to 0.2 µm, and even when the silver and silver chloride layer 242 is formed to have a smaller thickness than that of a conventionally known electrode, the corrosion prevention layer 244 formed on the silver and silver chloride layer 242 allows the non-polarizability of the non-polarizable electrode layer 24 to be maintained over the desired period of time as aforementioned. The silver and silver chloride layer 242 having such a thickness allows the electrode 1 to have excellent X-ray transmittance. In particular, the electrode 1 having the silver and silver chloride layer 242 with a thickness of 0.35 µm or less can sufficiently transmit X-rays, and can be configured not to interfere with the observation of internal organs using X-ray images. That is, the electrode 1 is a radiolucent electrode, and can be particularly suitable for use in X-ray examinations for children and fetuses having small internal organs.

The thickness of the silver and silver chloride layer 242 can be calculated as an average thickness by cross-sectional observation with a scanning electron microscope (SEM). Examples of a specific measurement method include a method in which the conductive gel layer 26 is removed from the electrode 1; a piece is cut out of the electrode layer

20 by, for example, microtome; the cross section of the cut piece is observed by an SEM at a magnification of 50000 to 100000 times; the thickness of the silver and silver chloride layer 242 is measured at a plurality of given positions (for example 9 positions); and an arithmetic average value of the measured thicknesses is used as the average thickness.

When the thickness of the silver and silver chloride layer 242 is set to the above value, the mass (or number of moles) of silver included in the silver and silver chloride layer 242 is generally 0.525 to 31.5 µg, preferably 0.525 to 10.5 µg, more preferably 0.525 to 5.25 µg, further preferably 0.525 to 3.68 µg, still further preferably 0.84 to 2.1 µg per unit area (mm$^2$) of the silver and silver chloride layer 242. The mass of silver can be measured, for example, as follows. First, as a method for preparing a measurement sample, the conductive gel layer 26 is removed from the electrode 1, a test piece having a silver mass of about 5 g is cut out of the electrode layer 20, and silver is extracted from the test piece using a nitric acid solution to obtain a silver extract liquid. Next, silver included in this silver extract liquid is quantified by, for example, the atomic absorption method, the ICP emission method, the X-ray fluorescence method, or the like. The method for quantifying silver is in principle the atomic absorption method. This quantitative analysis is performed multiple times, and the arithmetic average of these values is taken as the mass of silver included in the test piece.

The corrosion prevention layer 244 is formed to have a surface of the silver and silver chloride layer 242 covered with a polymer-based corrosion inhibitor. Covering the silver and silver chloride layer 242 with the corrosion prevention layer 244 allows the corrosion prevention layer 244 to block air from intruding into the silver and silver chloride layer 242 and thereby suppress deterioration of silver. The corrosion prevention layer 244 can suppress deterioration of silver resulting from the presence of the conductive gel layer 26. The silver and silver chloride layer 242 can include a part of the corrosion inhibitor, and the corrosion prevention layer 244 can include a part of silver and silver chloride.

The thickness of the corrosion prevention layer 244 needs to be set not to block or interfere with ion exchange between the silver and silver chloride layer 242 and the conductive gel layer 26 when the electrode 1 is used. In this regard, the thickness of the corrosion prevention layer 244 is set to 0.005 to 1.0 µm, preferably 0.01 to 0.6 µm, more preferably 0.015 to 0.5 µm. The thickness of the corrosion prevention layer 244 is calculated as an average thickness by cross-sectional observation with an SEM. Examples of a specific measurement method include a method in which the conductive gel layer 26 is removed from the electrode 1; a platinum layer is formed on the corrosion prevention layer 244 by the sputtering method; a piece is cut out of the electrode layer 20 by, for example, microtome; the cross section of the cut piece is observed by an SEM at a magnification of 10000 to 100000 times; the distance between the platinum layer formed by the sputtering method and the silver and silver chloride layer 242 is measured at a plurality of given positions (for example 9 positions); and an arithmetic average value of the measured thicknesses is used as the average thickness.

The polymer based corrosion inhibitor is used to form a film on the surface of the silver and silver chloride layer 242 to prevent corrosion of silver. The polymer-based corrosion inhibitor of this embodiment includes a resin and a thermosetting agent.

Examples of the corrosion inhibitor include VM-AL, VM-C, VM-TOP, and NCU-30 (B), which are manufactured by Dainichiseika Color & Chemicals Mfg. Co., Ltd.

In terms of being excellent in preventing corrosion of silver, examples of the resin include one, or two or more selected from the group consisting of a polyester-based resin, a urethane-based resin, an acrylic resin, an epoxy-based resin, a melamine-based resin, a styrene-based resin, a polyamide-based resin, a siloxane-based resin, a vinyl chloride-based resin, a vinyl acetate-based resin, a cellulose-based resin, a phenol-based resin, and the like. In terms of weather resistance, it is preferable that the resin include one, or two or more selected from the group consisting of a polyester-based resin, an acrylic resin, a urethane-based resin, an epoxy-based resin, a melamine-based resin, and a cellulose-based resin.

The mass ratio of the resin in the corrosion inhibitor is generally 80 to 99.9%, preferably 85 to 99%, more preferably 90 to 95%.

Examples of the thermosetting agent include a commonly available thermosetting agent, such as one, or two or more selected from the group consisting of an isocyanate-based thermosetting agent, an epoxy-based thermosetting agent, an imidazole-based thermosetting agent, and the like. In terms of weather resistance and reactivity, it is preferable that the thermosetting agent include an isocyanate-based thermosetting agent. Examples of the isocyanate-based thermosetting agent include a TDI (tolylene diisocyanate) based agent, an XDI (xylene diisocyanate) based agent, an MDI (methylene diisocyanate) based agent, and an HMDI (hexamethylene diisocyanate) based agent.

The mass ratio of the thermosetting agent in the corrosion inhibitor is generally 0.1 to 20%, preferably 1 to 15%, more preferably 5 to 10%.

The conductive gel layer 26 is a layer that brings the electrode 1 into contact with the surface of the skin. The conductive gel layer 26 includes, as an electrolyte, an alkali metal halide such as sodium chloride or potassium chloride. A conventionally known gel layer can be used for the conductive gel layer 26.

Figure 1B:
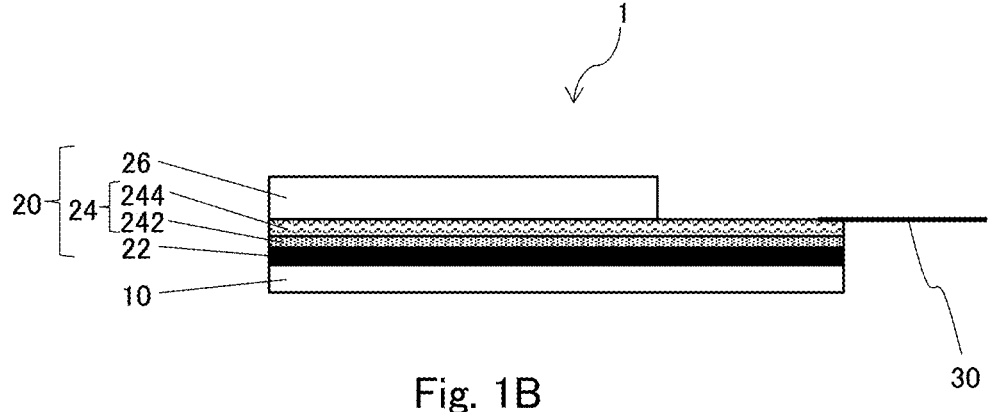
FIG. 1B is a schematic view showing a sectional structure of a configuration in which a lead wire is fixed to a position different from the lead wire in FIG. 1A.
Figure 1C:
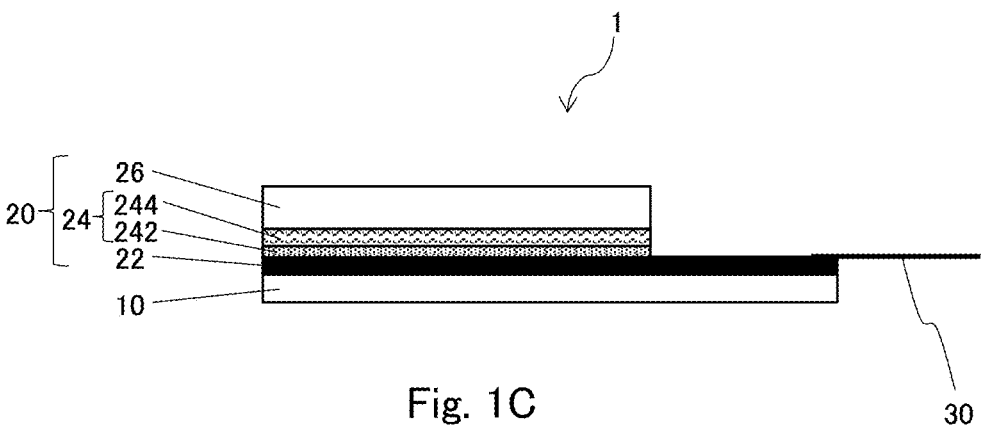
FIG. 1C is a schematic view showing a sectional structure of a configuration in which a lead wire is fixed at a position still different from the lead wires in FIG. 1A and FIG. 1B.

A conventionally known lead wire can be used for the lead wire 30, which includes a wire having a metal conductor covered with a covering material, or a wire having a conductor formed of a bundle of carbon fibers covered with a covering material. The lead wire 30 can have any configuration as long as it has one end electrically connected to the polarizable electrode layer 22. For example, in FIG. 1A, one end of the lead wire 30 is fixed to be sandwiched between the non-polarizable electrode layer 24 and the conductive gel layer 26. In FIG. 1B, one end of the lead wire 30 is fixed to contact a surface of the non-polarizable electrode layer 24 on a side on which the conductive gel layer 26 is formed, and no conductive gel layer 26 is formed at the position at which the one end is fixed. In FIG. 1C, one end of the lead wire 30 is fixed to contact a surface of the polarizable electrode layer 22 on a side on which the silver and silver chloride layer 242 is formed, and neither the non-polarizable electrode layer 24 nor the conductive gel layer 26 is formed at the position at which the one end is fixed.

Next, a method for producing the electrode 1 will be described.

The method for producing the electrode 1 includes: a polarizable electrode layer forming step S1 of forming the polarizable electrode layer 22 on one surface of the substrate 10; and a laminating step S2 of forming the non-polarizable electrode layer 24 on the surface of the polarizable electrode layer 22.

The polarizable electrode layer forming step S1 is a step of forming the polarizable electrode layer 22 by coating a surface of the substrate 10 with a carbon paste that includes graphite and/or carbon powder and an organic solvent in addition to the resin, followed by removing the organic solvent by drying.

The laminating step S2 includes: a silver thin film forming step 21 of forming a silver thin film on the surface of the polarizable electrode layer 22 formed in the polarizable electrode forming step S1; a covering step S22 of covering the silver thin film with a polymer-based corrosion inhibitor to form the corrosion prevention layer 244; and a chlorination treatment step S23 of converting a part of silver into silver chloride.

The silver thin film forming step S21 is a step of forming a silver thin film by the plating method. The plating method includes the wet plating method and the dry plating method. Examples of the wet plating method include the electrolytic plating method and the electroless plating method, and examples of the dry plating method include a vacuum vapor deposition method and the sputtering method. Among these thin film forming methods, the dry plating method is preferable and the vacuum vapor deposition method is further preferable in terms of being capable of suppressing the production cost of the electrode 1.

When the vacuum vapor deposition method is employed, the silver thin film is generally formed at a pressure of $1 \times 10^{-2}$ Pa or less and a crucible temperature of 900 to 1600° C.

The covering step S22 is a step of forming the corrosion prevention layer 244 by applying the polymer-based corrosion inhibitor to the entire area of the surface of the silver thin film, followed by heating and drying to cure the thermosetting agent included in the corrosion inhibitor.

The chlorination treatment step S23 is a step of forming the silver thin film into the silver and silver chloride layer 242 by immersing the silver thin film and the corrosion prevention layer 244 with an aqueous sodium hypochlorite solution to thereby convert a part of silver into silver chloride. After the immersion, the silver and silver chloride layer 242 and the corrosion prevention layer 244 are generally washed with water and further allowed to dry for removing the water thereon, in order to remove excess aqueous sodium hypochlorite solution. As a method for converting a part of silver into silver chloride, the electrolytic method or chlorine vapor deposition in which a saline solution or hydrochloric acid is used can be employed, and the electrolytic method is preferable when the corrosion prevention layer 244 is set to have a relatively large thickness. After the silver thin film forming step S21, the surface of the silver thin film can be subjected to chlorine vapor deposition, in which case the chlorination treatment step S23 can be omitted.

The effective chlorine concentration of the aqueous sodium hypochlorite solution is generally set to 0.5 to 12%. The duration of immersion in the aqueous sodium hypochlorite solution is generally set to 10 seconds to 5 minutes, and the immersion temperature is generally set to 20 to 50° C. At this time, the corrosion prevention layer 244 having a thickness as aforementioned allows chloride ions to pass therethrough to come into contact with silver, a part of which is converted into silver chloride.

As water used for washing, distilled water or ion-exchanged water is preferably used.

As described above, an electrode 1 according to this embodiment includes: a polarizable electrode layer 22; and a non-polarizable electrode layer 24 laminated on the polarizable electrode layer 22, in which the non-polarizable electrode layer 24 includes silver, silver chloride, and a corrosion inhibitor for the silver, and the corrosion inhibitor is a polymer-based corrosion inhibitor.

Such a configuration in which the non-polarizable electrode layer 24 includes the polymer-based corrosion inhibitor can suppress deterioration of silver. Even when the amount of silver used is reduced, this configuration allows the polymer-based corrosion inhibitor to suppress deterioration of silver, and can thus maintain non-polarizability of the non-polarizable electrode layer 24. Accordingly, the electrode excellent in storage stability and capable of reducing the amount of silver used is provided.

The electrode 1 is preferably configured such that the corrosion inhibitor includes a resin and a thermosetting agent.

Such a configuration in which the corrosion inhibitor includes the resin and the thermosetting agent allows the electrode to be more excellent in storage stability, and reduces the greater amount of silver used.

The electrode 1 is preferably configured such that the resin includes a polyester-based resin.

Such a configuration in which the resin includes the polyester-based resin allows the electrode to be further excellent in storage stability, and further reduces the amount of silver used.

The electrode 1 is preferably configured such that the thermosetting agent includes an isocyanate-based thermosetting agent.

Such a configuration in which the thermosetting agent includes the isocyanate-based curing agent allows the electrode to be still further excellent in storage stability, and still further reduces the amount of silver used.

The electrode 1 is preferably configured such that the non-polarizable electrode layer 24 includes a plating film of the silver formed on a surface of the polarizable electrode layer 22.

Such a configuration in which the non-polarizable electrode layer 24 includes the silver plating film can further reduce the amount of silver used.

The electrode 1 is preferably a biological electrode.

Such a configuration in which the amount of silver used is reduced to thereby allow the electrode to have excellent radiolucency does not interfere with the observation of internal organs using X-ray images.

As described above, one embodiment has been described as an exemplification, but the electrode according to the present invention is not limited to the configuration of the above embodiment. Further, the electrode according to the present invention is not limited by the aforementioned operational effects, either. Various modifications can be made to the electrode according to the present invention without departing from the gist of the present invention.

EXAMPLES

Hereinafter, the present invention will be further described by way of Examples.

Example 1

A conductive carbon paste (UCC-2, manufactured by Nippon Graphite Industries, Co., Ltd.) is applied to a PET film as a substrate, followed by being allowed to dry at 120°

C. to form a polarizable electrode layer on one surface of the substrate. The thickness of the polarizable electrode layer was 5 μm. On the surface of the polarizable electrode layer, a silver thin film having a thickness of 0.2 μm was formed by vacuum vapor deposition. Subsequently, a corrosion inhibitor including a polyester resin and an isocyanate-based thermosetting agent was applied as a polymer-based corrosion inhibitor to the entire area of the surface of the silver thin film, and the thermosetting agent was cured by heating and drying to form a corrosion prevention layer. The substrate on which the layers were formed as aforementioned was cut into pieces of 50 mm×100 mm, each of which was then subjected to chlorination treatment by being immersed in an aqueous sodium hypochlorite solution (code No. 197-02206 manufactured by Wako Pure Chemical Industries, Ltd.) for 3 minutes to convert a part of silver into silver chloride, thereby forming a silver and silver chloride layer. After being thoroughly washed with distilled water, the cut piece was allowed to dry in a constant temperature bath set at 120° C. to remove water. Each of the cut substrates was further cut into pieces of 15×30 mm, and conductive gel layers (CR-H manufactured by Sekisui Kasei Co., Ltd.) each having a size of 15×15 mm were attached respectively to the cut pieces on a side on which each of the corrosion prevention layers was formed so as to allow a short side of each of the cut pieces and an end edge of the conductive gel layer to overlap each other, thereby obtaining electrodes.

Example 2

Figure 2:
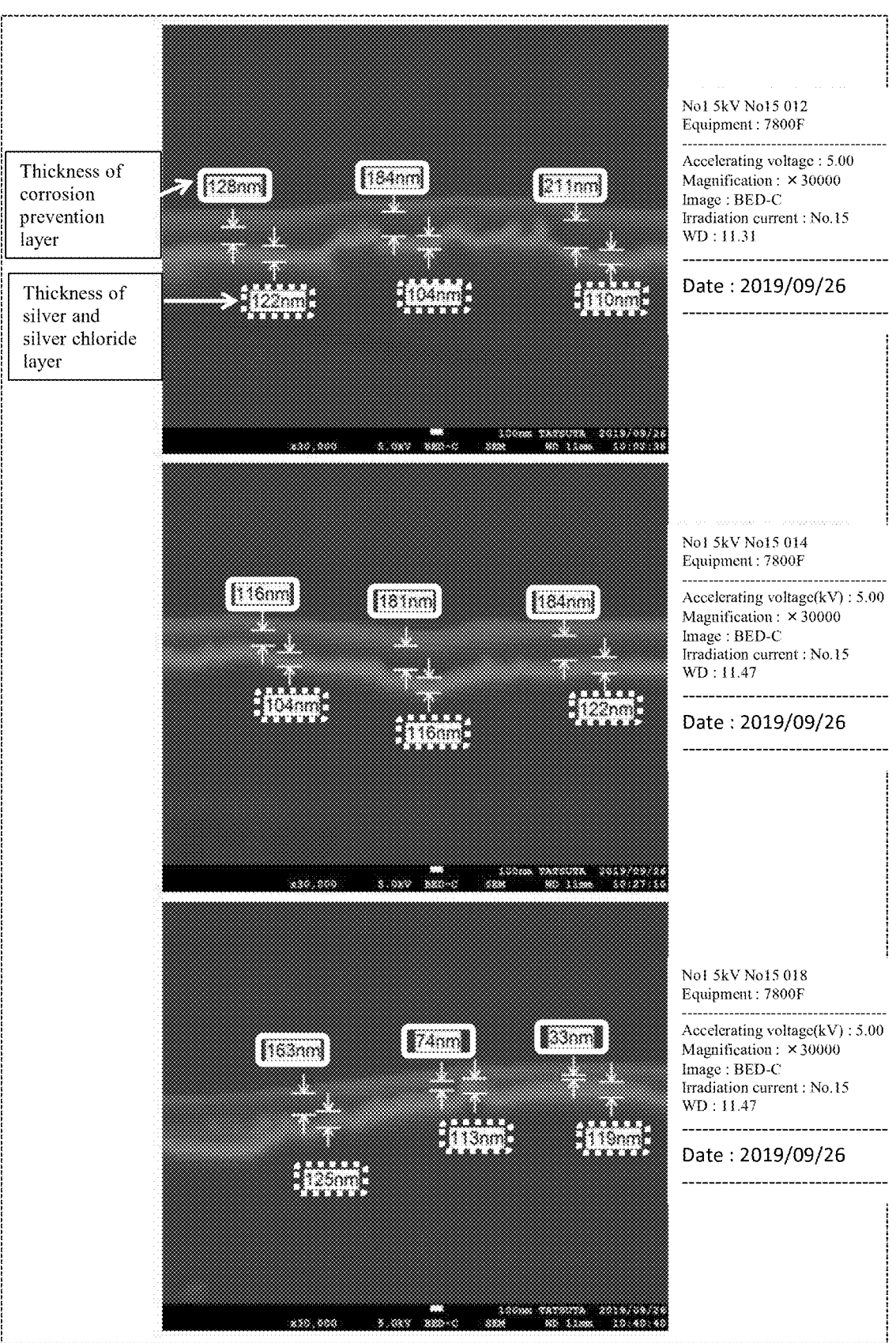
FIG. 2 is a view showing SEM images of sectional structures of an electrode of Example 2.

Electrodes were prepared in the same manner as in Example 1, except that the thickness of the silver thin film was set to 0.1 μm. As shown in FIG. 2, the thickness of the corrosion prevention layer was measured at 9 positions using an SEM, and ranged from 0.033 to 0.211 μm (average thickness: 0.14 μm). The thickness of the silver and silver chloride layer ranged from 0.104 to 0.125 μm (average thickness: 0.12 μm).

Example 3

Electrodes were prepared in the same manner as in Example 1, except that the thickness of the polarizable electrode layer was set to 20 μm and the thickness of the silver thin film was set to 0.1 μm.

Comparative Example 1

Electrodes were prepared in the same manner as in Example 1, except that no corrosion prevention layer was formed and an aqueous sodium hypochlorite solution (code No. 197-02206 manufactured by Wako Pure Chemical Industries, Ltd.) diluted by 10 times was used for immersion for 1 minute for chlorination treatment.

Comparative Example 2

Electrodes were prepared in the same manner as in Example 1, except that no corrosion prevention layer is formed and an aqueous sodium hypochlorite solution (code No. 197-02206 manufactured by Wako Pure Chemical Industries, Ltd.) diluted by 10 times was used.
[Evaluation Method 1]

Figure 3:
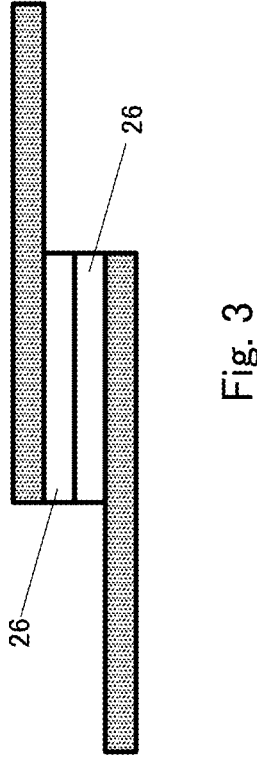
FIG. 3 is a schematic view showing a state of electrodes in Examples when being evaluated.

The electrodes prepared in each of above Examples and Comparative Examples were placed with their conductive gel layers attached to each other as shown in FIG. 3, and were subjected to impedance measurement and the defibrillation recovery test in accordance with the method of ANSI/AAMI EC12:2000.

[Evaluation Method 2]

The electrodes prepared in each of Examples and Comparative Examples were placed in an aluminum pack, which was stored in a constant temperature bath set to 57° C. Storage at 57° C. for 10 weeks is equivalent to storage at room temperature for 2 years. After a specific period of time elapsed, the electrodes in each of Examples and Comparative Examples were taken out of the aluminum pack, and were subjected to impedance measurement and the defibrillation recovery test in accordance with the method of ANSI/AAMI EC12:2000 in the same manner as in Evaluation Method 1 above.

Figure 4:
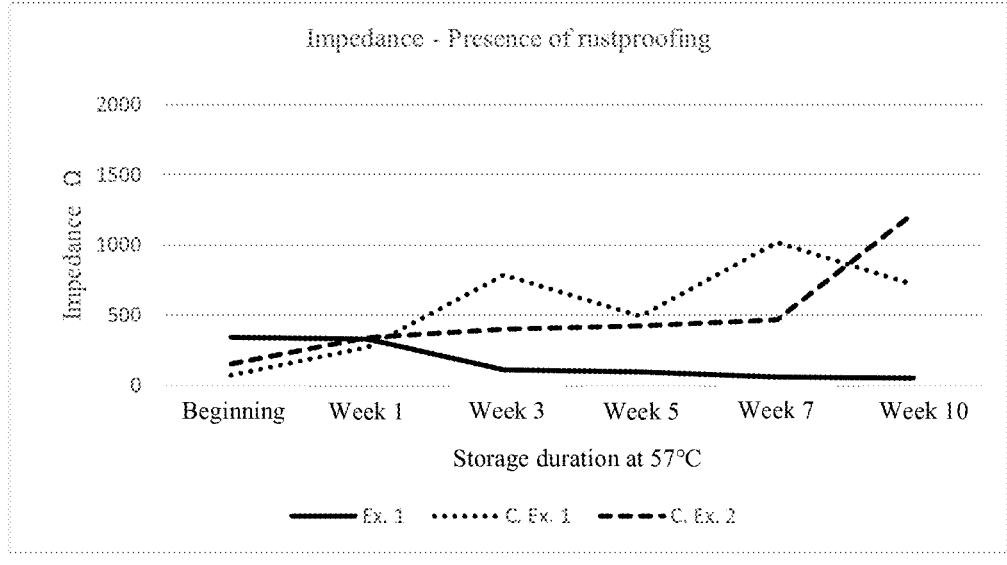
FIG. 4 shows graphs showing the effectiveness of a corrosion inhibitor in Examples.
Figure 4:
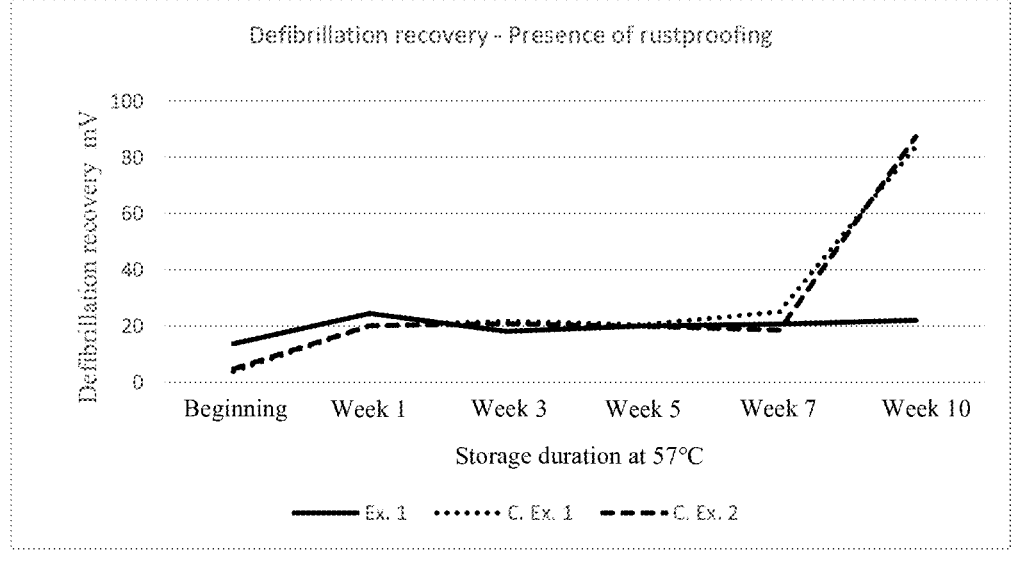

As shown in FIG. 4, the electrodes in Example 1 showed an impedance of 500Ω or less and also showed good polarization voltage absolute values in the defibrillation recovery test both at the beginning (Evaluation Method 1) and over 10 weeks (Evaluation Method 2). Further, the electrodes in Example 1 showed a tendency of gradual decrease in impedance from the beginning of storage, and were found to have excellent storage stability. In contrast, the electrodes in each of Comparative Example 1 and Comparative Example 2 showed a tendency of increase in impedance from the beginning of storage, and were found to have poor storage stability and to be unsuitable for long-term storage.

Figure 5:
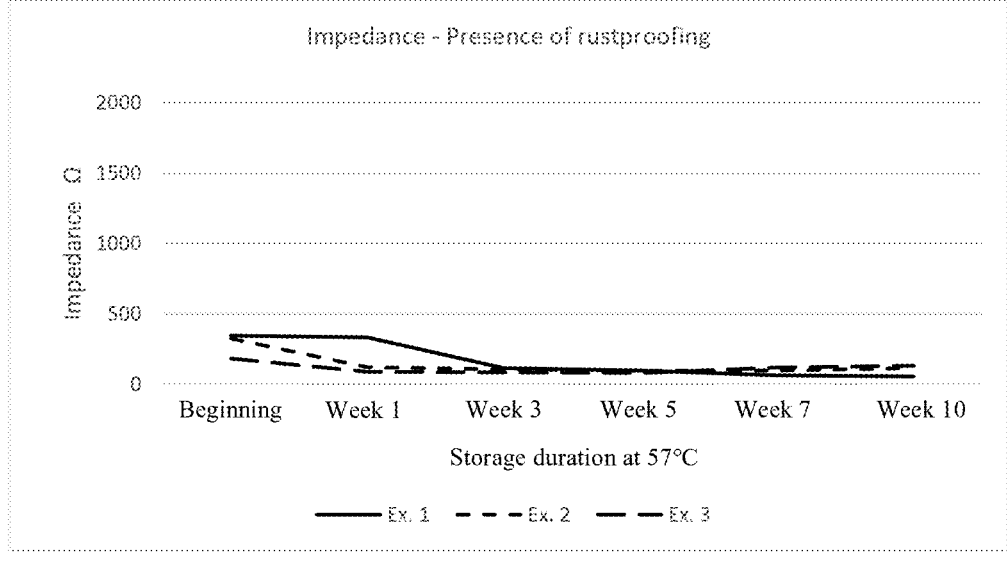
FIG. 5 shows graphs showing the effect of the thicknesses of thin silver films in Examples.
Figure 5:
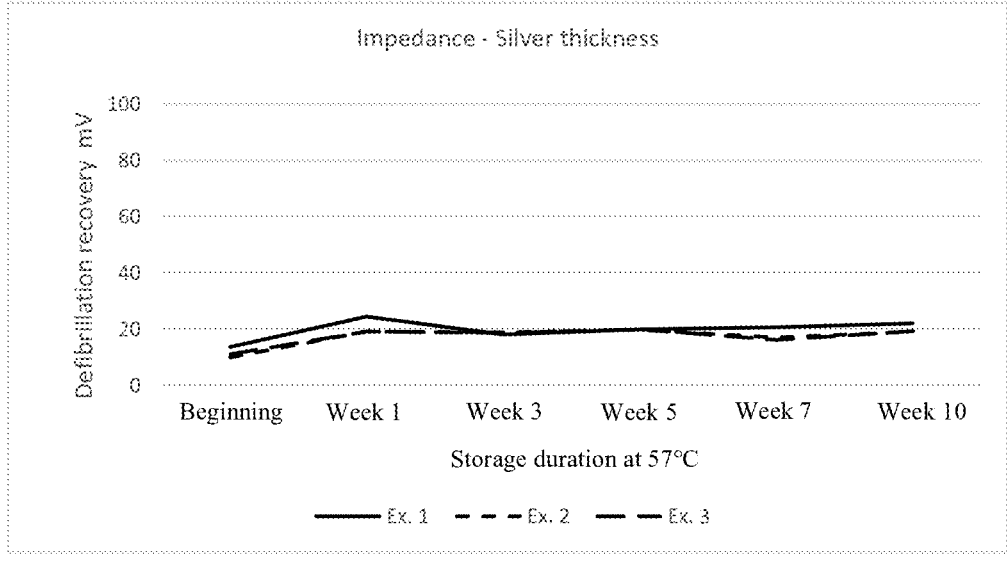

Even in the case where the thickness of the silver thin film was further reduced to 0.1 μm, the electrodes of Examples 2 and 3 were found to have the same performance as that of the electrodes of Example 1 with the silver thin film having a thickness of 0.2 μm, as shown in FIG. 5. These results suggest that electrodes capable of further reducing the amount of silver used while maintaining storage stability can be provided.

REFERENCE SIGNS LIST

1: Electrode
10: Substrate
20: Electrode layer
22: Polarizable electrode layer
24: Non-polarizable electrode layer
242: Silver and silver chloride layer
244: Corrosion prevention layer
26: Conductive gel layer

The invention claimed is:

1. An electrode comprising:

a polarizable electrode layer;

a non-polarizable electrode layer laminated on the polarizable electrode layer; and a conductive gel layer laminated on the non-polarizable electrode layer such that the conductive gel layer is configured to contact a skin surface, wherein the non-polarizable electrode layer comprises a silver and silver chloride layer laminated on the polarizable electrode layer, and a corrosion prevention layer covering the silver and silver chloride layer, wherein the corrosion prevention layer is made of a polymer-based corrosion inhibitor and has a thickness of 0.015 μm to 0.5 μm, wherein the corrosion inhibitor comprises at least one compound selected from a polyester-based resin, a urethane-based resin, an acrylic resin, an epoxy-based resin, a melamine-based resin, a cellulose-based resin, or combinations of two or more thereof, and wherein the corrosion prevention layer is configured to be ion-permeable such that ion exchange occurs between the silver and silver chloride layer and the conductive gel layer.

2. The electrode according to claim 1, wherein the corrosion inhibitor comprises a thermosetting agent.

3. The electrode according to claim 2, wherein the thermosetting agent comprises an isocyanate-based thermosetting agent.

4. The electrode according to claim 1, wherein the non-polarizable electrode layer comprises a plating film of the silver formed on a surface of the polarizable electrode layer.

5. The electrode according to claim 1, the electrode being a biological electrode.

6. The electrode according to claim 1, wherein the silver and silver chloride layer of the non-polarizable electrode layer has a thickness of 0.05 μm to 0.35 μm.

7. The electrode according to claim 1, wherein the non-polarizable electrode layer comprises a plating film of the silver formed on a surface of the polarizable electrode layer, and wherein the silver and silver chloride layer of the non-polarizable electrode layer has a thickness of 0.05 μm to 0.35 μm.

* * * * *